United States Patent
Ruellan et al.

(10) Patent No.: US 9,733,223 B2
(45) Date of Patent: Aug. 15, 2017

(54) GAS CONCENTRATION SENSOR WITH A SUSPENDED STRUCTURE

(71) Applicant: COMMISSARIAT A L'ENERGIE ATOMIQUE ET AUX ENE ALT, Paris (FR)

(72) Inventors: Jeremie Ruellan, Grenoble (FR); Laurent Duraffourg, Voiron (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 179 days.

(21) Appl. No.: 14/619,656

(22) Filed: Feb. 11, 2015

(65) Prior Publication Data

US 2015/0226713 A1    Aug. 13, 2015

(30) Foreign Application Priority Data

Feb. 13, 2014   (FR) ...................................... 14 51134

(51) Int. Cl.
*G01N 7/00*   (2006.01)
*G01N 30/62*   (2006.01)
(Continued)

(52) U.S. Cl.
CPC ............. *G01N 30/62* (2013.01); *B01D 53/02* (2013.01); *G01N 27/18* (2013.01)

(58) Field of Classification Search
USPC ..................................... 73/23.35, 23.4, 25.01
See application file for complete search history.

(56) References Cited

U.S. PATENT DOCUMENTS

| 4,665,366 A * | 5/1987 | Macovski ............ G01R 33/446 |
| | | 324/307 |
| 7,531,136 B2 * | 5/2009 | Besnard ............... G01N 27/127 |
| | | 422/82.01 |

(Continued)

FOREIGN PATENT DOCUMENTS

FR    2 824 911 A1    11/2002
GB    2 426 592 A     11/2006
(Continued)

OTHER PUBLICATIONS

U.S. Appl. No. 14/519,390, filed Oct. 21, 2014.
(Continued)

*Primary Examiner* — Lisa Caputo
*Assistant Examiner* — Nasir U Ahmed
(74) *Attorney, Agent, or Firm* — Oblon, McClelland, Maier & Neustadt, L.L.P.

(57) ABSTRACT

A concentration sensor for at least one given gas comprising at least one suspended structure (2) with respect to a support, said suspended structure (2) being of an electrically conductive material and said structure having a low heat response time, means for biasing said suspended element (2) and means (8) for measuring the variation of the electric voltage at the terminals of the suspended structure (2), the biasing means (6) being formed by an alternating current source the intensity of which heats the suspended structure (2) and the frequency of which gives rise to a phase shift between a signal of the biasing means and a signal measured by the measuring means, and means for determining a phase shift variation due to a gas concentration variation and means for determining the concentration variation of said gas from the phase variation.

20 Claims, 4 Drawing Sheets (51) Int. Cl.
*B01D 53/02* (2006.01)
*G01N 27/18* (2006.01)

(56) References Cited

U.S. PATENT DOCUMENTS

| | | | | |
|---|---|---|---|---|
| 7,963,147 | B2* | 6/2011 | Jun | G01N 27/128 73/25.01 |
| 8,030,690 | B2 | 10/2011 | Ollier et al. | |
| 8,117,898 | B2* | 2/2012 | Viens | G01N 27/18 73/25.03 |
| 8,310,320 | B2 | 11/2012 | Duraffourg et al. | |
| 8,361,200 | B2* | 1/2013 | Sayari | B01D 53/02 95/139 |
| 8,536,962 | B2 | 9/2013 | Bilhaut et al. | |
| 8,783,107 | B2 | 7/2014 | Robert et al. | |
| 2003/0033861 | A1 | 2/2003 | Eisenschmid et al. | |
| 2009/0250310 | A1* | 10/2009 | Popp | F16H 61/30 192/85.18 |
| 2010/0154510 | A1 | 6/2010 | Viens et al. | |
| 2010/0219489 | A1 | 9/2010 | Duraffourg et al. | |
| 2012/0272742 | A1 | 11/2012 | Andreucci et al. | |
| 2013/0144542 | A1 | 6/2013 | Ernst et al. | |
| 2013/0170517 | A1 | 7/2013 | Duraffourg et al. | |
| 2013/0214644 | A1 | 8/2013 | Hentz et al. | |
| 2014/0076024 | A1 | 3/2014 | Duraffourg et al. | |
| 2014/0079091 | A1 | 3/2014 | Ruellan et al. | |
| 2014/0148575 | A1 | 5/2014 | Forge et al. | |

FOREIGN PATENT DOCUMENTS

| | | |
|---|---|---|
| WO | WO 01/44547 A2 | 6/2001 |
| WO | WO 2004/077037 A1 | 9/2004 |
| WO | WO 2007/117156 A1 | 10/2007 |

OTHER PUBLICATIONS

French Preliminary Search Report issued Jul. 30, 2014, in Patent Application No. FR 1451134, filed Feb. 13, 2014 (with English Translation of Category of Cited Documents).
Andrew P. Lee, et al., "Temperature modulation in semiconductor gas sensing", Sensors and Actuators B, vol. 60, 1999, pp. 35-42.
R. Triantafyllopoulou, et al., "Alternative micro-hotplate design for low power sensor arrays", Microelectronic Engineering, vol. 83, 2006, pp. 1189-1191.
E. Mile, et al., "In-plane nanoelectromechanical resonators based on silicon nanowire piezoresistive detection", Nanotechnology, vol. 21, 2010, 7 pages.
Ph. Robert, et al., "M&NEMS: A new approach for ultra-low cost 3D inertial sensor", IEEE Sensors, 2009, pp. 963-966.
J. F. Creemer, et al., "MEMS Hotplates with TiN as a Heater Material", Sensors, 2005, pp. 330-333.
F. T. Zhang, et al., "A micro-Pirani vacuum gauge based on micro-hotplate technology", Sensors and Actuators A, vol. 126, 2006, pp. 300-305.
Li, et al., "A novel SOI Pirani sensor with triple heat sinks", Procedia Chemistry, vol. 1, 2009, pp. 160-163.
R. Puers, et al., "The NanoPirani-an extremely miniaturized pressure sensor fabricated by focused ion beam rapid prototyping", Sensors and Actuators A, vols. 97-98, 2002, pp. 208-214.
U.S. Appl. No. 14/429,676, filed Mar. 19, 2015, Ruellan, et al.
Extended European Search Report issued Jun. 29, 2015 in Patent Application No. 15154415.2 (with English translation of Category of Cited Documents).

* cited by examiner

GAS CONCENTRATION SENSOR WITH A SUSPENDED STRUCTURE

TECHNICAL FIELD AND PRIOR ART

The present invention relates to a gas concentration sensor with a suspended structure.

There are gas concentration sensors using the measurement of a heat exchange between the sensor body and the gas medium wherein the sensor is disposed. The variation in the fluid medium changes heat exchanges, by measuring the change in the heat exchanges, the gas concentration of the gas medium can be determined.

Document WO2001/044547 describes a TCD ("Thermal Conductivity Detectors") sensor using the variation in the heat conductivity to determine the composition of the gas environment in which it is disposed. This sensor is disposed at the output of a chromatography column. This TCD sensor comprises an elongate support plate, a heating element located on the support plate. The voltage variation is measured at the terminals of the heated support plate to determine the electrical resistance variation which depends on the temperature of the support plate and which is representative of the heat exchanges between the support plate and the gas environment; these heat exchanges depend on the composition of the gas environment. Such a sensor involves a complex manufacture because it requires making the support plate and then making the heating element.

The detection is made by measuring the amplitude of the electrical resistance variation. But phenomena can disturb the measurement in the case of an amplitude measurement. In particular, in nanostructures, since the area/volume ratio is high, undesired surface phenomena, for example adsorption phenomena, can play a role on the electrical resistance value of the device and thus on the amplitude measurement.

Further, generally, it is intended to reduce the size of sensors to facilitate the integration thereof and increase the number of application fields.

DISCLOSURE OF THE INVENTION

Consequently, one purpose of the present invention is to provide a device for measuring the concentration of a gas not having the abovementioned drawbacks, and to provide in particular a more robust device for measuring the gas concentration, i.e. offering less sensitivity to parasitic phenomena than the amplitude measuring devices.

It is also a purpose of the present invention to provide a thermal flow sensor with a simpler manufacturing than that of sensors of the state of the art.

The previously set out purpose is achieved by a device for measuring the concentration of at least one given gas, the measuring device comprising a suspended structure, means for dynamically biasing said suspended structure forming dynamic excitating means and means for measuring the response signal which is the dynamic variation of the electric voltage at the terminals of the suspended structure, and means for processing said response signal. Under the effect of the dynamic excitating signal, the suspended structure is heated, its temperature will then vary by heat exchange with the gas environment whose composition changes. The excitation frequency is selected such that a phase shift exists between the excitation signal and the response signal. The variation in this phase shift is a function of the thermal conductivity of the gas and the heat capacity of the gas. During the change in the gas concentration in the gas environment, the phase shift varies. From the measurement of the phase shift variation, it is possible to determine the concentration of the gas analyte.

By "dynamic bias", it is meant the application of an alternating electric current of a given period and by "dynamic variation of the electric voltage", the voltage variation due to the variation of the electrical resistance of the suspended structure which results from the time variation of the temperature of the suspended structure.

In one embodiment, the voltage excitation frequency is set close to or equal to half the thermal cut-off frequency of the system in a given state, for example in the absence of analyte. The phase shift variation is measured, and from this variation, the propagation time of the gas mixture can be determined and the concentration of gas analyte deduced.

In another embodiment, the phase shift is set, and the variation in the cut-off frequency is measured. Preferably, a phase locked loop (PLL) is used wherein the phase value is corrected in real time, an operation can then be made at the greatest sensitivity.

The fact of using the phase shift variation between the excitation signal and the response signal is very interesting because the inventors have determined that the measurement of this phase shift variation was not affected by parasitic phenomena, unlike the amplitude measurement.

The suspended structure has preferably sufficiently small dimensions to have a very low thermal response time, thus allowing the use of a modulated signal sufficiently high in comparison with the measurement time, for example from a few hundred Hz to a few hundred kHz. This is for example a nanometer structure, such as a nanowire or a structure forming a grid.

By virtue of the invention, more reliable measurements than amplitude measuring devices are obtained since the device according to the invention is hardly, or even not sensitive to parasitic phenomena.

Further, the application of dynamic excitation signals enables the sensor to be made less sensitive to slow drifts, for example to drifts of the medium temperature.

The measuring device according to the invention has also a high resolution of the system temperature measurement.

This invention further allows to make high performance detectors having very small sizes which are co-integrable with microelectronic technologies and CMOS (VLSI) compatible.

Such a sensor is particularly interesting as a gas concentration sensor used in and/or at the output of a gas chromatography micro-column.

One subject-matter of the present invention is a concentration sensor for at least one given gas species comprising at least a suspended structure in a gas environment with respect to a support, said suspended structure being of an electrically conductive material, means for biasing said suspended element and means for measuring the variation of the electric voltage at the terminals of the suspended structure, the biasing means being formed by an alternating current source the intensity of which provides heating of the suspended structure by Joule effect and the frequency of which is such that it gives rise to a phase shift between a signal generated by the biasing means and a signal measured by the measuring means, and means for determining a phase shift variation due to a concentration variation of the gas species and means for determining the concentration variation of said gas species from the phase shift variation.

The gas environment comprises a carrier gas and the gas species to be measured. Besides, at a given time, the sensor can measure only one gas species at a time. To measure different gas species, the species are previously separated for example by a chromatography column disposed upstream from the sensor.

Preferably, said structure has a low thermal response time and in particular lower than 100 ms.

In one embodiment, the frequency of the biasing means is set.

The voltage frequency of the biasing means is advantageously close to or equal to half the cut-off frequency of a heat transfer function of the sensor in a given gas environment.

The cut-off frequency can be that of the heat transfer function of the sensor in a gas environment in the absence of the gas species the concentration of which is desired to be measured.

In another embodiment, the concentration sensor comprises a phase locked loop in which a phase shift value is set, wherein a value of the phase shift variation due to the concentration variation of the gas species is measured and wherein the frequency of the biasing means is changed such that the measured phase shift is equal to the set phase shift, the change in the frequency being used to determine the concentration variation.

For example, the suspended structure is formed by at least one nanowire. The nanowire has preferably a length lower than 1 mm and a cross-section lower than 1 μm×1 μm.

In an advantageous example, the concentration sensor comprises several suspended structures, each of the suspended structures being biased and a signal being measured at the terminals of each of the suspended structures by the measuring means, these signals being averaged.

Another subject-matter of the invention is a device for measuring a concentration of at least one gas species contained in a gas environment comprising a chromatography column and at least one concentration sensor according to the invention, the sensor being disposed at the output of or within the chromatography column.

Another subject-matter of the present invention is a method for measuring the concentration of at least one gas species using a suspended structure in a gas environment, said method comprising the steps of:
 applying a biasing signal of the suspended structure of an electrically conductive material at a given frequency so as to heat the suspended structure and such that a phase shift exists between the biasing signal and a temperature variation of the suspended structure,
 measuring the phase shift variation,
 determining the concentration variation of the gas species.

The voltage frequency is preferably set to half the cut-off frequency of a heat transfer function characteristic of the heat exchanges of the suspended structure with the gas environment for a given gas environment. For example, in the given gas environment, the concentration of gas species is null.

In a measuring mode, the phase shift is set to a control value, the phase shift variations relative to the control value are measured during the concentration variation of the gas species and the frequency is changed so as to bring the phase shift value closer to the control value.

Preferably, since the gas species is in mixture with a carrier gas so as to form the gas environment, the carrier gas is selected so as to have a heat propagation time different from that of the gas species.

BRIEF DESCRIPTION OF THE DRAWINGS

The present invention will be better understood using the description that follows and the appended drawings wherein.

DETAILED DISCLOSURE OF PARTICULAR EMBODIMENTS

The gas concentration sensor according to the invention is intended to measure the concentration of at least one gas analyte mixed with a carrier gas. The concentration mentioned in the description that follows is thus that of an analyte.

In the description that follows, the phase shift designates the phase shift between the response or output signal and the excitation signal. The response signal which can also be referred to as the output signal is the temperature variation of the suspended structure, this variation being obtained by measuring the electrical resistance variation of the suspended structure, which itself is obtained by measuring the voltage variation at the terminals of the suspended structure.

Figure 1:
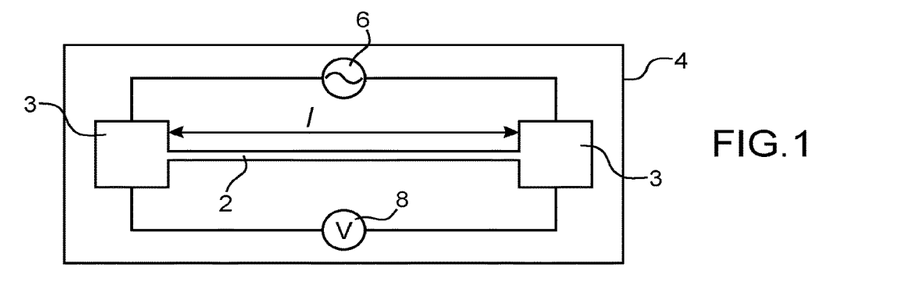
FIG. 1 is a schematic representation of an example of sensors with a nanowire.

In FIG. 1, an exemplary measuring device according to the invention can be seen, comprising a suspended structure 2 with respect to a support 4 at its two longitudinal ends. In the example represented, the suspended structure is formed by a nanowire 2 anchored to the support by anchoring pads 3 forming contact pads.

According to the invention, the suspended structure is such that it enables the structure to be current biased in order to be able to heat it and/or to be able to measure a detection signal at its terminals, and has sufficiently small dimensions to have a low thermal response time, for example lower than 10 ms, allowing a quick overall response time of the sensor.

In the present application, by "suspended structure having a low heat response time", it is intended a suspended structure which is thermalized within 100 ms, and preferentially within 10 ms, i.e. the temperature of which is changed to reach another homogeneous value on the entire structure within 100 ms and preferentially within 10 ms under the effect of an external element, for example the concentration of the analyte to be measured. The response time is mainly set by the carrier gas and by the configuration of the structure, for example the air gap between the suspended structure and the support and the geometrical characteristics of the suspended structure.

In the case of a silicon nanowire, its length is advantageously lower than 1 mm and its width and the thickness of the nanowire are advantageously between 1 nm and 1 μm.

Preferably, the suspended structure is of P-doped single crystal silicon, but it can also be made of N-doped single crystal silicon, in another N- or P-doped semi-conductor or in a metal or metal alloy for example of silicide for example NiSi, PtSi . . . . The suspended structure can also be made using a bilayer assembly formed by an electrically and thermally insulating material and a metal or metal alloy.

In the description that follows, use is made of the phrase "the terminals of the nanowire", to refer to the contact pads of the nanowire on the support which are generally formed on the anchoring pads of the nanowire onto the support.

The measuring device also comprises dynamic or modulated excitating means formed by alternating bias means 6 linked to the nanowire 2 and means for detecting the voltage variation at the terminals of the nanowire, formed for example by a voltmeter 8.

The alternating current imposed by the excitating means 6 provides dynamic heating of the nanowire by Joule effect. The application of a modulated excitation signal is made possible thanks to the very small dimensions of the suspended element 2, the latter having thus a very low thermal inertia and therefore a very quick thermal response.

Preferably, the voltage frequency of the biasing means is close to or equal to half the cut-off frequency of the thermal transfer function of the suspended structure which characterizes the ability of the suspended structure to exchange heat with the gas mixture.

The operation of the measuring device of FIG. 1 will now be explained.

The suspended nanowire 2 is disposed in a gas mixture to be analysed. The gas mixture is for example formed by a carrier gas and an analyte the concentration of which is desired to be determined.

The nanowire 2 is heated by flowing the alternating current therethrough. By Joule effect, this generates thermal power causing it to be self-heated. The temperature rise of the nanowire depends on the heat transfers from the nanowire to the gas environment and to the anchorings. These are mainly the transfers with the environment which control heating of the nanowire.

In a first embodiment, the voltage excitation frequency is set to a value such that a phase shift exists between the temperature variation of the nanowire and the current variation, this frequency is however sufficiently low for the nanowire temperature to have time to vary.

The voltage excitation frequency is preferably close to or equal to ½ the cut-off frequency of the thermal transfer function of the system in a given state, for example in the absence of gas species in the gas environment. At this frequency in a given reference state, for example the state in the absence of gas species, a non-zero phase shift, called a reference phase shift, appears. When the concentration of the gas species varies relative to the concentration of the reference state, the phase shift between the excitation signal and the response signal increases and is sufficiently great to be measurable.

Preferably, the voltage excitation frequency is between ¼ of the cut-off frequency and the cut-off frequency.

When the analyte concentration in the gas environment is changed, the thermal conductivity and heat capacity of the gas environment are changed. As a result, the heat exchanges between the nanowire and the gas environment are changed. The thermal response time of the system is thus changed. When the thermal excitation signal is sinusoidal and is made according to a time constant close to the thermal response time of the system, a change in this response time causes a phase shift variation of the response signal. The measurement of the phase shift variation between the measured phase shift and the reference phase shift enables the gas concentration to be deduced as will be explained below.

In the rest of the application, the phase shift variation corresponds to the difference between the measured phase shift and the non-zero reference phase shift. The reference phase shift can be that of the response signal for a null or non-null concentration.

In the case where the sensor is associated with a chromatography column, variations relative to a baseline for which the concentration value of gas species to be analysed is null will be detected. The reference state is then that of null gas species concentration.

The temperature variations of the system are measured via electrical resistance variations in the nanowire, these electrical resistance variations being due to the dependency of the electrical resistivity of a material to temperature. The heat resistance is in turn determined measuring the voltage at the terminals of the nanowire 2 by the voltmeter.

By determining the local temperature of the nanowire, it is possible to deduce the analyte concentration(s) in the carrier gas.

It will now be explained how to determine the phase shift variation, and then the concentration from the phase.

The Joule effect power produced by the nanowire is equal to:

$$P_J = R_0 I^2$$

$R_0$ is the initial electrical resistance of the nanowire.

The current source 6 biases the nanowire with an alternating current $I=I_0 \cos(\omega t)$ (I) of an angular frequency $\omega$, as a result there is a power generation at the angular frequency $2\omega$:

$$P_J = \frac{R_0 I_0^2}{2}[1 + \cos(2\omega t)].$$

The nanowire temperature then depends on the excitation frequency and can be written as:

$$T = T_{thermostat} + \Delta T(\omega t)$$

$T_{thermostat}$ being the temperature of the support and anchoring pads.

The temperature variations $\Delta T(\omega t)$ depend on a thermal transfer function $H_{th}$, which characterizes the ability of the system to exchange the heat thereof with the gas mixture. In the present case, it comprises a term related to exchanges by silicon, and a term related to exchanges by the gas. Besides, it contains a frequency component related to taking heat capacities into account.

The thermal transfer function is in the form:

$$H_{th}(j\omega) = \frac{\Delta T_d}{P_J} = \frac{R_{th}}{1 + jR_{th}C_{th}\omega_{th}}$$

The power generation in the nanowire generates temperature variations in the nanowire comprising a static component and a component at the angular frequency $2\omega$ and the phase and amplitude of which depend on the thermal transfer function of the system.

The temperature variation can be written as:

$$\Delta T = \Delta T_s + \Delta T_d \cos(\omega_{th} t + \phi) \qquad (II)$$

Where $\omega_{th}=2\omega$ is the thermal signal angular frequency, $\Delta T_s$ and $\Delta T_d$ are the amplitude of the static and dynamic variations respectively, and $\phi$ is the phase shift of the response signal.

If the transfer function is known, it is possible to deduce the phase shift of the temperature variations.

Thus:

$$\phi = -\arctan(R_{th}C_{th}\omega_{th})$$

It is observed that the phase of the response signal depends on the resistivity and heat capacity of the gas. If the phase shift is known, the product $R_{th}C_{th}$ is known.

Figure 2:
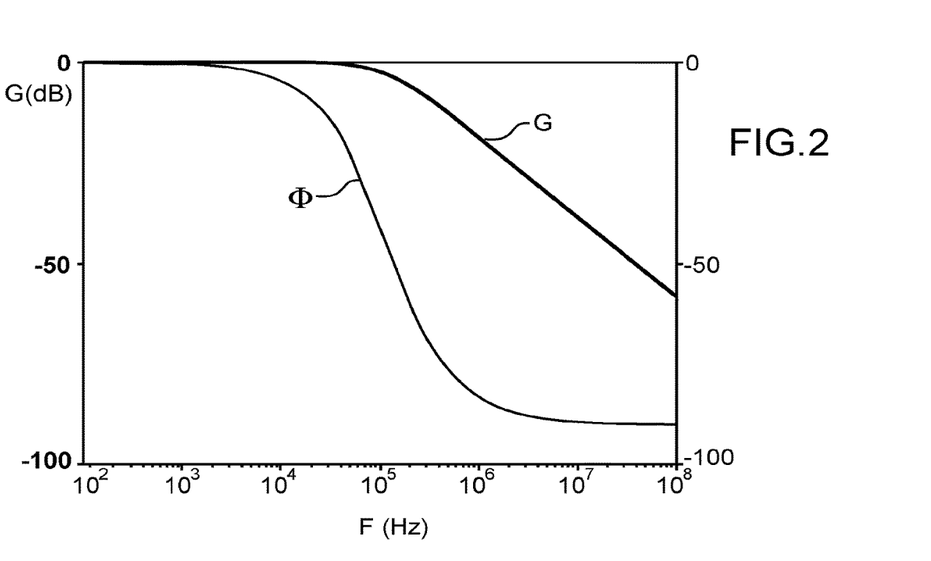
FIG. 2 is a representation of the heat transfer function of the system according to the invention.

In FIG. 2, the representation of the heat transfer function $H_{th}$ represented in terms of gain G in dB and phase $\phi$ in ° as a function of the frequency in Hz can be seen. The gain G corresponds to the heat attenuation.

The amplitude and phase of the temperature variations thus depend on the excitation frequency and the parameters of the transfer function. In the present case, the transfer function is of the $1^{st}$ order low-pass filter type. As a result, therefore, when the excitation signal is slow (low frequency) relative to the thermal response time of the system, the system follows the temperature variations of the excitation signal, no phase appears. If the excitation signal is too quick relative to the thermal response time of the system, the temperature of the system does not vary.

The resonance frequency of the transfer function varies with the conductivity and heat capacity of the gas which change because of its concentration variation. By selecting a voltage excitation frequency close to or equal to the ½ cut-off frequency of the system in the absence of the gas species, the temperature of the system varies with an amplitude reduced relative to a nearly steady state and with a phase shift. At this frequency, the phase shift variation is significant.

The method for determining the phase will now be described.

The temperature variations of the system are determined by measuring the electrical resistance of the nanowire. This dependency is expressed by the thermal coefficient of resistivity (TCR).

The value of the electrical resistance as a function of the temperature is written as:

$$R=R_0(1+\text{TCR}\cdot\Delta T)$$

The voltage at the terminals of the nanowire is written as:

$$V_{sin\,w}=RI=R_0(1+\text{TCR}\cdot\Delta T)I$$

and depends on the temperature.

Thus, by measuring the voltage at the terminals of the nanowire and if the TCR of the nanowire is known, it is possible to know the temperature of the system.

The electrical resistance of the nanowire varies at the same frequency and with the same phase shift as the heat signal.

By replacing $\Delta T$ and $I$ by the relationships (II) and (I) respectively, the following is obtained:

$$V_{sin\,w}=RI=R_0(1+\text{TCR}\cdot(\Delta T_s+\Delta T_d\cos(\omega_{th}t+\phi)))I_0\cos(\omega t),$$

It is reminded that $\omega_{th}=2\omega$ Thus it results from the linearization of the previous equation that:

$$V_{sin\,w}=R_0I_0\cos(\omega t)+R_0I_0\cdot\text{TCR}\cdot\Delta T_s\cos(\omega t)+1/2R_0I_0\cdot\text{TCR}\cdot\Delta T_d\cos(3\omega t+\phi)+1/2R_0I_0\cdot\text{TCR}\cdot\Delta T_d\cos(\phi)$$

the component $3\omega$ of this signal, which corresponds to the $3^{rd}$ harmonic of the signal, being equal to:

$$V_{3\omega}=1/2R_0I_0\cdot\text{TCR}\cdot\Delta T_d\cos(3\omega t+\phi)$$

This voltage of an angular frequency $3\omega$ is the image of the temperature variations of the nanowire.

By filtering and synchronous detection, the phase shift of the signal $3\omega$ is determined.

It is then possible to calculate the product $R_{th}C_{th}$ from the phase shift value determined above.

Besides, as indicated above, the characteristic heat propagation time $\tau_{th}$ in an air gap/gas gap is determined by its thermal resistivity and heat capacity. This time is also called the thermal response time and characterizes the thermalization time of the gas. When the gas concentration varies, the characteristic time varies.

The characteristic time is written as:

$$\tau_{th}=\frac{1}{f_{th}}=2\pi R_{th}C_{th}$$

with $$R_{th}=\rho_{th}\frac{g}{S}$$

and $$C_{th}=c_v\rho gS$$

where $$\rho_{th}=\frac{1}{k_{th}}$$

is the thermal resistivity of the gas, g and S are respectively the width of the air gap and the exchange area (cross-section of the gap), $c_v$ is the heat capacity of the gas and $\rho$ its density.

Thus, since the product $R_{th}C_{th}$ has been determined, the characteristic time $\tau_{th}$ can be calculated, and since the gas is known, its concentration can be deduced therefrom.

Besides, the gas kinetics is such that:

$$k_{th} \propto c_v\rho\lambda(v)$$

where $\lambda$ is the mean free path of the gas molecules and (v) their average velocity.

Finally:

$$\tau_{th} \propto \frac{g^2}{\lambda(v)}$$

The gas the concentration of which is desired to be measured is generally mixed with a carrier gas, for example helium or hydrogen.

At ambient temperature and pressure, the following table shows the value of the ratio $$\frac{g^2}{\lambda(v)}$$

for different gases for a 1 μm gap.

| Gas | Helium | Hydrogen | NH$_2$ | Toluene | Pentane |
|---|---|---|---|---|---|
| 1/λ(v) (s) | 4.02.10$^{-9}$ | 3.42.10$^{-9}$ | 22.10$^{-9}$ | 130.10$^{-9}$ | 106.10$^{-9}$ |

In the case where the analyte has a long response time, and since helium and hydrogen have short propagation times, i.e. they are quickly thermalized, it is possible to observe a strong variation in the thermal response time of the system when the analyte concentration varies.

Generally, a carrier gas having a propagation time very different from the propagation times of the analyte(s) is selected.

The determination of the phase shift variation and the determination of the concentration are made by means of an electronic system in a computer.

Figure 3A:
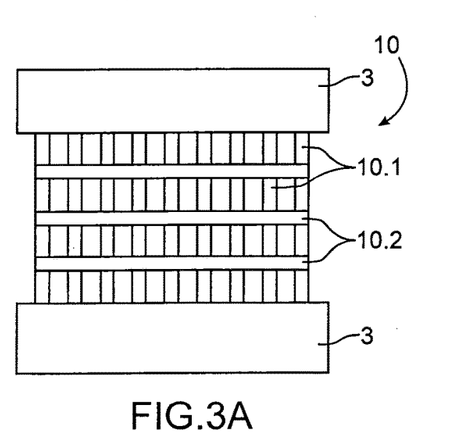
FIGS. 3A to 3C are top view schematically represented of exemplary embodiments of suspended structures according to the invention.
Figure 3B:
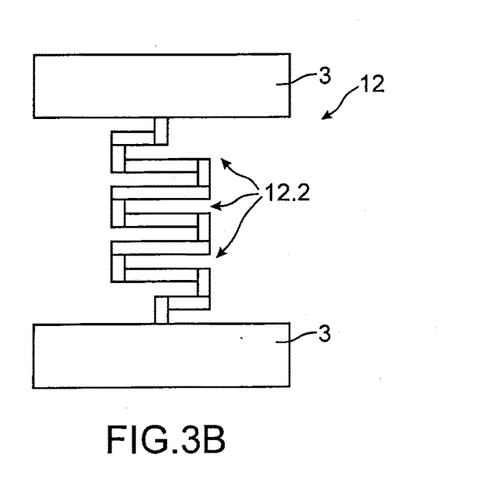
Figure 3C:
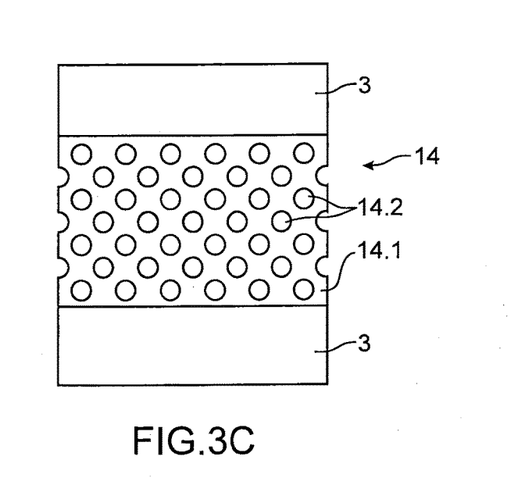

In FIGS. 3A to 3C, exemplary suspended structures that can be implemented in the concentration sensor according to the invention can be seen.

In FIG. 3A, the suspended structure 10 is in the form of a grid formed by a plurality of first nanowires 10.1 parallel to each other and suspended between two anchoring pads 3. The measurements performed on each nanowire are averaged, which enables the system noise to be reduced. Preferably and as is represented, the structure comprises a plurality of second nanowires 10.2 transverse to the first nanowires 10.1 and which mechanically link the first wires to each other, insuring a better mechanical rigidity of the entire structure, avoiding in particular a contact between the first wires.

In FIG. 3B, the suspended structure 12 is formed by a succession of crenels 12.2 suspended between two anchoring pads.

In FIG. 3C, the suspended structure 14 is formed by a plate 14.1 pierced with staggered holes 14.2, this relative arrangement of the holes being not limiting.

The examples of FIGS. 3B and 3C allow to offer a system having a greater sensitivity to the gas by offering a higher exchange area.

Combining these structures can be contemplated, for example in the structure of FIG. 3A to replace the straight nanowires by the nanowires of FIG. 3B.

Advantageously, a measurement system comprising several sensors or several types of sensors can be provided in order to increase the resolution. Indeed, an event present on all the sensors will be considered as a signal whereas an event only present on a sensor will be able to be classified as a measuring artefact. This redundancy thus enables to make the measurement more robust and the signal to be more quickly separated from the noise and continuous background.

The suspended structure can be of silicon, preferably for operating temperatures which are not too high to avoid silicon oxidation.

Advantageously, the structure can be made in a composite manner with a silicon support, forming a mechanical support and a fine electrically conductive layer can be formed on the support, for example conformably deposited to the surface of the nanowires. Preferably, the material of the layer has a good TCR and a melting point as high as possible thus allowing high operating temperatures increasing the signal to noise ratio. For example, the conductive layer can be made of tungsten, chromium, nickel or TiN.

Preferably, the conductive layer also forms a silicon encapsulating layer thus limiting its oxidation at a high temperature.

Alternatively, structures could be made, enabling a piezoresistive transduction to be implemented. For example, by making a structure with several thin layers having different thermal expansion coefficients and comprising at least one piezoresistive material, a bimetal effect can appear. The bimetal effect could be exploited. Thus, a variation in the stresses in the thin layers would appear with the temperature variations of these layers. This variation in the stresses would cause by a piezoresistive effect a resistance variation which would be measured as explained above.

Advantageously, the sensor can be integrated in a circuit allowing a differential measurement, which enables the detection of phase variations to be improved by removing the common mode signals. For example, a Wheatstone bridge type connection can be used.

A differential amplifier can also advantageously be used to recover the signal at the output of this connection.

In another embodiment, the sensor is integrated to a locked loop enabling to operate at the greatest sensitivity. The loop is schematized in FIG. 5.

Figure 5:
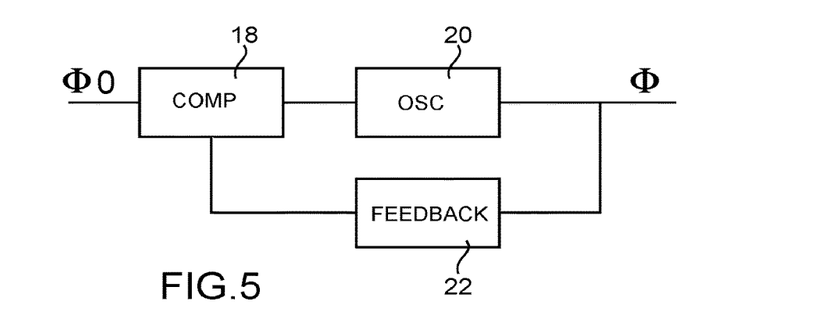
FIG. 5 is a schematic representation of an exemplary locked loop that can be implemented in the present invention.

For example, the phase shift value is set to $\phi_0$ by the user and a voltage controlled oscillator 20 delivers the excitation signal. The phase shift variation is measured, and then a comparison between the control value and the actual value of the phase shift is made in the comparator 18 and enables the frequency of this oscillator to be controlled in order to correct the phase shift value in real time by the feedback loop 22. Therefore, the phase shift variation is no longer measured, but rather a variation in the cut-off frequency is measured. As the variation in the cut-off frequency and phase shift is known, the product $R_{th}C_{th}$ can be determined from the relationship $\phi=-\arctan(R_{th}C_{th}\omega_{th})$. Then, the analyte concentration is determined in the same manner as with the phase shift variation.

An exemplary method for manufacturing a sensor according to the present invention will now be described.

In FIGS. 4A to 4H, schematic representations of different steps of the manufacturing method can be seen.

Figure 4A:
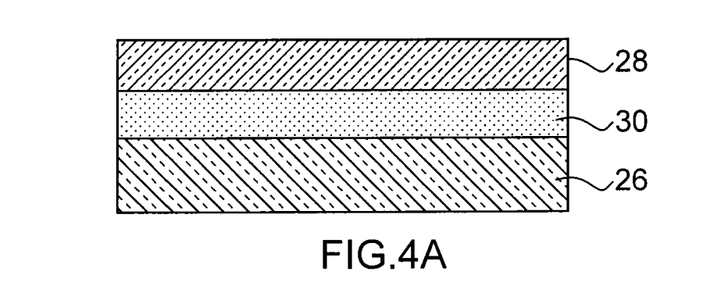
FIGS. 4A to 4H are schematic representations of different steps of an exemplary method for making a sensor according to the invention.

In the example described, a silicon on insulator (SOI) plate, represented in FIG. 4A, is used. The SOI substrate comprises a silicon layer 26, a single crystal silicon layer 28, the layers 26, 28 being separated by a $SiO_2$ layer 30. The single crystal silicon layer 28 forms the front face.

Figure 4B:
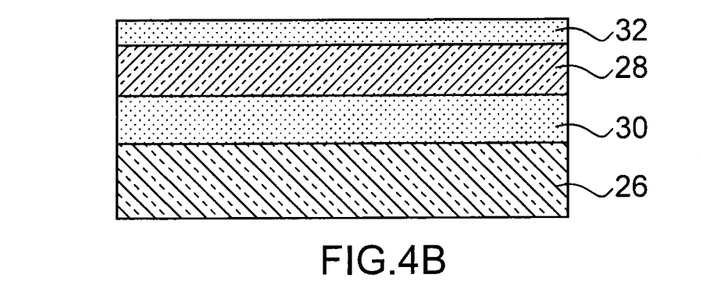

During a first step, a $SiO_2$ oxide layer 32 is deposited onto the layer 28. The resulting element is represented in FIG. 4B.

Figure 4C:
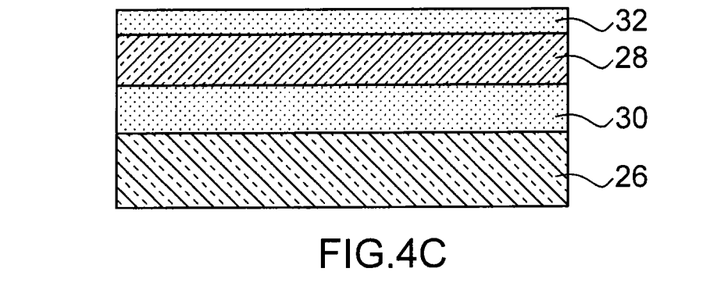

During a next step, a P++-doping is performed for example with boron, of the silicon layer 28 located between the oxide layer 30 and the oxide layer 32.

The doping through the oxide layer allows a more even distribution of the dopants in the layer 28. The doping obtained is in the order of $1.10^{19}$ at./cm$^3$). This doping has the effect to maximize the thermal coefficient of resistivity of silicon.

The resulting element is represented in FIG. 4C. The doping is symbolized by dots.

Figure 4D:
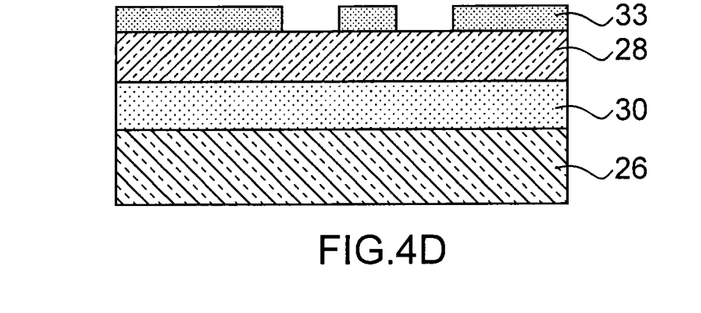

During a next step, the oxide layer 32 is withdrawn and a resin layer 33 is deposited, wherein the outlines of the patterns are defined in the resin 32 by lithography, for example deep-UV (DUV) lithography or hybrid DUV and electron beam (e-beam) lithography. These lithography methods are well known to those skilled in the art and will not be described in further detail. The e-beam lithography allows effects related to light diffraction upon etching nanometer devices to be avoided.

The resulted element is represented in FIG. 4D.

Figure 4E:
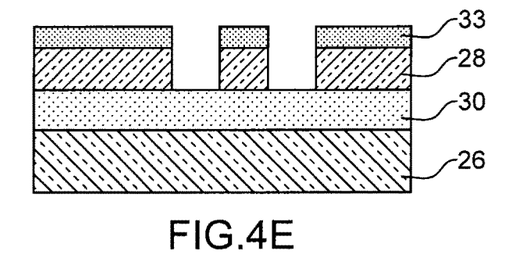

During a next step, the silicon layer is etched, for example by anisotropic RIE (Reactive Ion Etching).

The resulting element is represented in FIG. 4E.

Figure 4F:
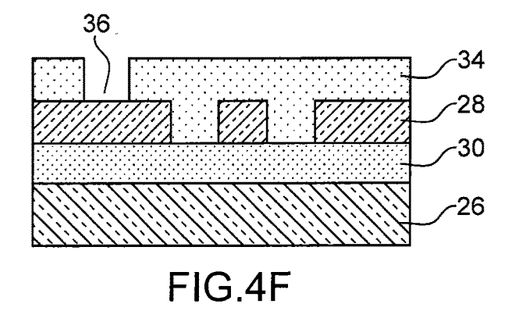

During a next step, a $SiO_2$ chemical deposition 34 is performed onto the etched silicon layer 28 which is then etched to bound the locations 36 of the electrical contacts, for example plasma etching.

Thus obtained element is represented in FIG. 4F.

Figure 4G:
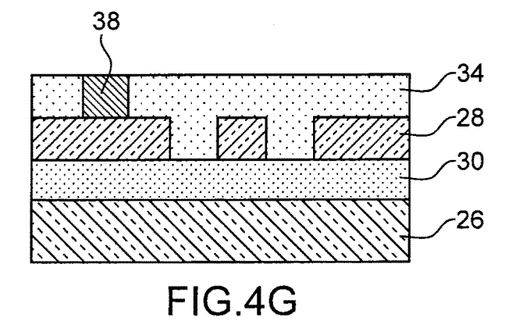

Then, the electrical contacts 38 are made by depositing for example aluminium, for example spray deposition.

The resulting element is represented in FIG. 4G.

Figure 4H:
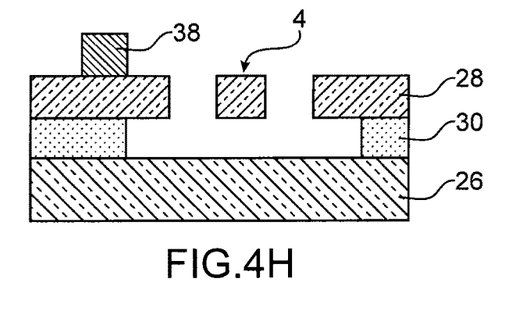

During a next step, the nanowire is released, for example by etching the layer 30, for example with vapour hydrofluoric acid.

The released structure is visible in FIG. 4H.

This gas concentration sensor is particularly suitable for being associated with gas chromatography micro-column. The sensor can be disposed at the output of or within the column. The column separates the different components of a mixture contained in a carrier gas, when the sensor is at the output, it sees different analytes successively and can measure the concentration of each of them. All of this thus forms a robust multigas concentration sensor.

The invention claimed is:

1. A concentration sensor for at least one gas species comprising:
   at least one suspended structure in a gas environment with respect to a support, said at least one suspended structure being of an electrically conductive material;
   a biasing circuit configured to bias said at least one suspended structure by providing an alternating current to a first terminal of said at least one suspended structure at a first end thereof and a second terminal of said at least one suspended structure at a second end thereof opposite the first end;
   a measuring circuit configured to measure variation of electric voltage at the first and second terminals of said at least one suspended structure;
   a first determination circuit configured to determine a variation of a phase shift between a signal generated by the biasing circuit to bias said at least one suspended structure and a signal measured by the measuring circuit that corresponds to the variation of the electric voltage at the first and second terminals, the variation of the phase shift being due to a concentration variation of the at least one gas species; and
   a second determination circuit configured to determine the concentration variation of the at least one gas species from the determined variation of the phase shift,
   wherein the biasing circuit includes an alternating current source configured to provide the alternating current, an intensity of which provides heating of said at least one suspended structure by Joule effect, and a frequency of which is such that it gives rise to the phase shift between the signal generated by the biasing circuit to bias said at least one suspended structure and the signal measured by the measuring circuit that corresponds to the variation of the electric voltage at the first and second terminals.

2. The concentration sensor according to claim 1, wherein the signal measured by the measuring circuit is equal to a $3\omega$ component.

3. The concentration sensor according to claim 2, wherein the $3\omega$ component is equal to $V_{3\omega}=1/2R_0I_0 \cdot TCR \cdot \Delta T_d \cos(3\omega t+\phi)$.

4. The concentration sensor according to claim 1, wherein said at least one suspended structure has a heat response time lower than 100 ms.

5. The concentration sensor according to claim 1, wherein the frequency of the biasing circuit is fixed.

6. The concentration sensor according to claim 5, wherein the frequency of the biasing circuit is close to or equal to half a cut-off frequency of a heat transfer function of the concentration sensor in the gas environment.

7. The concentration sensor according to claim 6, wherein the frequency of the biasing circuit is close to or equal to half the cut-off frequency of the heat transfer function of the concentration sensor in the gas environment in the absence of the at least one gas species, a concentration of which is desired to be measured.

8. The concentration sensor according to claim 1, further comprising a phase locked loop in which a phase shift value is set,
   wherein a value of the variation of the phase shift due to the concentration variation of the at least one gas species is measured, and
   wherein the frequency of the biasing circuit is changed such that the measured phase shift is equal to the set phase shift, the change in the frequency being used to determine the concentration variation.

9. The concentration sensor according to claim 1, wherein said at least one suspended structure includes at least one nanowire.

10. The concentration sensor according to claim 9, wherein the at least one nanowire has a length lower than 1 mm and a cross-section lower than 1 µm×1 µm.

11. The concentration sensor according to claim 1, wherein said at least one suspended structure includes several suspended structures, each of the suspended structures being biased, and a signal being measured at the first and second terminals of each of the suspended structures by the measuring circuit, whereupon these signals are averaged.

12. A device for measuring a concentration of the at least one gas species contained in the gas environment comprising:
   a chromatography column; and
   at least one concentration sensor according to claim 1, said at least one concentration sensor being disposed at an output of or within the chromatography column.

13. The concentration sensor according to claim 1, wherein the at least suspended structure consists of a single conductive material.

14. The concentration sensor according to claim 1,
   wherein the at least suspended structure is not configured to vibrate, and
   wherein the phase shift variation is caused by the concentration variation of the at least one gas species and not vibration of the at least one suspended structure.

15. The concentration sensor according to claim 1, wherein the variation in the phase shift constitutes a variation in cut-off frequency.

16. A method for measuring the concentration of at least one gas species using a suspended structure in a gas environment, said method comprising:
   applying a biasing signal to the suspended structure, which comprises an electrically conductive material, at a given frequency so as to heat the suspended structure and so as to create a phase shift between the biasing signal and a temperature variation of the suspended structure;
   measuring a variation of the phase shift; and
   determining a concentration variation of the at least one gas species,
   wherein the biasing signal is an alternating current signal applied to a first terminal of the suspended structure at a first end thereof and a second terminal of the suspended structure at a second end thereof opposite the first end.

17. The method for measuring the concentration of at least one gas species according to claim 16, wherein the suspended structure includes a biasing circuit, a frequency of the biasing circuit being set to half a cut-off frequency of a heat transfer function characteristic of heat exchanges of the suspended structure with the gas environment for a given gas environment.

18. The method for measuring the concentration of a gas species according to claim 17, wherein in the given gas environment, the concentration of the at least one gas species is null.

19. The method for measuring the concentration of at least one gas species according to claim 16,
   wherein the phase shift is set to a control value,
   wherein variations of the phase shift relative to the control value are measured during the concentration variation of the at least one gas species, and
   wherein the given frequency is changed so as to bring the phase shift closer to the control value.

20. The method for measuring the concentration of at least one gas species according to claim 16, wherein the at least one gas species is in a mixture with a carrier gas so as to form the gas environment, the carrier gas being selected so as to have a heat propagation time different from a heat propagation time of the at least one gas species.

* * * * *